United States Patent
De Vicente Fidalgo et al.

(10) Patent No.: US 9,469,644 B2
(45) Date of Patent: Oct. 18, 2016

(54) INHIBITORS OF BRUTON'S TYROSINE KINASE

(71) Applicant: Hoffmann-La Roche Inc., Nutley, NJ (US)

(72) Inventors: Javier De Vicente Fidalgo, Foster City, CA (US); Romyr Dominique, Ridgewood, NJ (US); Francisco Javier Lopez-Tapia, Honolulu, HI (US); Sung-Sau So, Verona, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 14/768,688

(22) PCT Filed: Mar. 3, 2014

(86) PCT No.: PCT/EP2014/054017
§ 371 (c)(1),
(2) Date: Aug. 18, 2015

(87) PCT Pub. No.: WO2014/135473
PCT Pub. Date: Sep. 12, 2014

(65) Prior Publication Data
US 2016/0002243 A1    Jan. 7, 2016

Related U.S. Application Data

(60) Provisional application No. 61/772,938, filed on Mar. 5, 2013.

(51) Int. Cl.
*A61K 31/52* (2006.01)
*C07D 473/34* (2006.01)
*C07D 473/16* (2006.01)

(52) U.S. Cl.
CPC ............. *C07D 473/34* (2013.01); *A61K 31/52* (2013.01); *C07D 473/16* (2013.01)

(58) Field of Classification Search
CPC ... C07D 473/16; C07D 473/34; A61K 31/52
USPC ............................ 544/264; 514/263.1, 263.2
See application file for complete search history.

(56) References Cited

U.S. PATENT DOCUMENTS

2012/0122840 A1* 5/2012 Kumar ................ C07D 519/00
514/210.21

OTHER PUBLICATIONS

Ling-Kuen Huang et al, "An efficient synthesis of substituted cytosines and purines under focused microwave irradiation," Tetrahedron 63 (2007) 5323-5327.*
The English translation of the Chinese Office Action, issued on Mar. 25, 2016, in the corresponding Chinese Application No. 201480011832.1.
Leese et al., "Potential anti-purines. Part II. The synthesis of 6- and 9-substituted purines and 8-azapurines," J. Chem. Soc., 1958, 4107-4110.
ASC, RN 1096287-15-8, Registry on STN, Jan. 27, 2009.

* cited by examiner

*Primary Examiner* — Kamal Saeed
*Assistant Examiner* — Janet L Coppins

(57) ABSTRACT

This application discloses compounds according to generic Formula (I) wherein all variables are defined as described herein, which inhibit BTK. The compounds disclosed herein are useful to modulate the activity of BTK and treat diseases associated with excessive BTK activity. The compounds are further useful to treat inflammatory and auto immune diseases associated with aberrant B-cell proliferation such as rheumatoid arthritis. Also disclosed are compositions containing compounds of Formula (I) and at least one carrier, diluent or excipient.

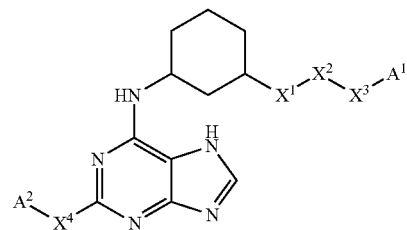

(I)

17 Claims, No Drawings

INHIBITORS OF BRUTON'S TYROSINE KINASE

CROSS-REFERENCE TO RELATED APPLICATIONS

This application is a National Stage Application of PCT/EP2014/054017 filed Mar. 3, 2014, which claims priority from U.S. Provisional Patent Application No. 61/772,938, filed on Mar. 5, 2013. The priority of both said PCT and U.S. Provisional Patent Application are claimed. Each of the prior mentioned applications is hereby incorporated by reference herein in its entirety.

FIELD OF THE INVENTION

The present invention relates to the use of novel compounds which inhibit BTK and are useful for the treatment of auto-immune and inflammatory diseases caused by aberrant B-cell activation.

BACKGROUND OF THE INVENTION

Protein kinases constitute one of the largest families of human enzymes and regulate many different signaling processes by adding phosphate groups to proteins (T. Hunter, Cell 1987 50:823-829). Specifically, tyrosine kinases phosphorylate proteins on the phenolic moiety of tyrosine residues. The tyrosine kinase family includes members that control cell growth, migration, and differentiation. Abnormal kinase activity has been implicated in a variety of human diseases including cancers, autoimmune and inflammatory diseases. Since protein kinases are among the key regulators of cell signaling they provide a target to modulate cellular function with small molecular kinase inhibitors and thus make good drug design targets. In addition to treatment of kinase-mediated disease processes, selective and efficacious inhibitors of kinase activity are also useful for investigation of cell signaling processes and identification of other cellular targets of therapeutic interest.

There is good evidence that B-cells play a key role in the pathogenesis of autoimmune and/or inflammatory disease. Protein-based therapeutics that deplete B cells such as Rituxan are effective against autoantibody-driven inflammatory diseases such as rheumatoid arthritis (Rastetter et al. Annu Rev Med 2004 55:477). Therefore inhibitors of the protein kinases that play a role in B-cell activation should be useful therapeutics for B-cell mediated disease pathology such as autoantibody production.

Signaling through the B-cell receptor (BCR) controls a range of B-cell responses including proliferation and differentiation into mature antibody producing cells. The BCR is a key regulatory point for B-cell activity and aberrant signaling can cause deregulated B-cell proliferation and formation of pathogenic autoantibodies that lead to multiple autoimmune and/or inflammatory diseases. Bruton's Tyrosine Kinase (BTK) is a non-BCR associated kinase that is membrane proximal and immediately downstream from BCR. Lack of BTK has been shown to block BCR signaling and therefore inhibition of BTK could be a useful therapeutic approach to block B-cell mediated disease processes.

BTK is a member of the Tec family of tyrosine kinases, and has been shown to be a critical regulator of early B-cell development and mature B-cell activation and survival (Khan et al. Immunity 1995 3:283; Ellmeier et al. J. Exp. Med. 2000 192:1611). Mutation of BTK in humans leads to the condition X-linked agammaglobulinemia (XLA) (reviewed in Rosen et al. New Eng. J. Med. 1995 333:431 and Lindvall et al. Immunol. Rev. 2005 203:200). These patients are immunocompromised and show impaired maturation of B-cells, decreased immunoglobulin and peripheral B-cell levels, diminished T-cell independent immune responses as well as attenuated calcium mobilization following BCR stimulation.

Evidence for a role for BTK in autoimmune and inflammatory diseases has also been provided by BTK-deficient mouse models. In preclinical murine models of systemic lupus erythematosus (SLE), BTK-deficient mice show marked amelioration of disease progression. In addition, BTK-deficient mice are resistant to collagen-induced arthritis (Jansson and Holmdahl Clin. Exp. Immunol. 1993 94:459). A selective BTK inhibitor has been demonstrated dose-dependent efficacy in a mouse arthritis model (Z. Pan et al., Chem. Med Chem. 2007 2:58-61).

BTK is also expressed by cells other than B-cells that may be involved in disease processes. For example, BTK is expressed by mast cells and BTK-deficient bone marrow derived mast cells demonstrate impaired antigen induced degranulation (Iwaki et al. J. Biol. Chem. 2005 280:40261). This shows BTK could be useful to treat pathological mast cells responses such as allergy and asthma. Also monocytes from XLA patients, in which BTK activity is absent, show decreased TNF alpha production following stimulation (Horwood et al. J Exp Med 197:1603, 2003). Therefore TNF alpha mediated inflammation could be modulated by small molecular BTK inhibitors. Also, BTK has been reported to play a role in apoptosis (Islam and Smith Immunol. Rev. 2000 178:49) and thus BTK inhibitors would be useful for the treatment of certain B-cell lymphomas and leukemias (Feldhahn et al. J. Exp. Med. 2005 201:1837).

SUMMARY OF THE INVENTION

The present application provides the BTK inhibitor compounds of Formula I, methods of use thereof, as described herein below:

The application provides a compound of Formula I,

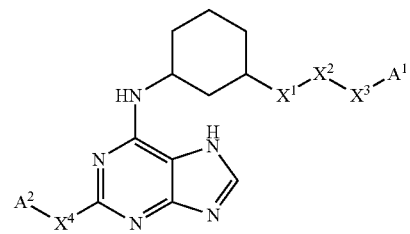

wherein:
$A^1$ is H or $A^{1'}$;
$A^{1'}$ is lower alkyl or phenyl, optionally substituted with one or more $A^{1''}$;
  each $A^{1''}$ is independently halo or lower alkyl;
$A^2$ is H or $A^{2'}$;
$A^{2'}$ is heteroaryl, optionally substituted with lower alkyl;
$X^1$ is —NH, C(=O), or absent;
$X^2$ is —NH, C(=O), or absent;
$X^3$ is lower alkylene or absent; and
$X^4$ is —NH or absent;
or a pharmaceutically acceptable salt thereof.

The application provides a method for treating an inflammatory and/or autoimmune condition comprising administering to a patient in need thereof a therapeutically effective amount of the compound of Formula I.

The application provides a pharmaceutical composition comprising the compound of Formula I, admixed with at least one pharmaceutically acceptable carrier, excipient or diluent.

DETAILED DESCRIPTION OF THE INVENTION

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "-----" drawn through a bond each refer to the point of attachment of a functional group or other chemical moiety to the rest of the molecule of which it is a part. Thus, for example:

$MeC(=O)OR^4$ wherein

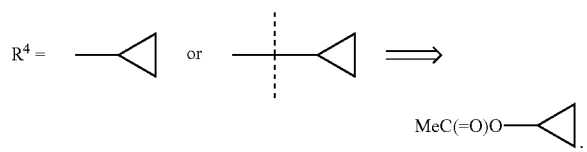

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen atom or a substituent.

The phrase "optional bond" means that the bond may or may not be present, and that the description includes single, double, or triple bonds. If a substituent is designated to be a "bond" or "absent", the atoms linked to the substituents are then directly connected.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Certain compounds of Formulae I may exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH-⇌-C(—OH)=CH—), amide/imidic acid (—C(=O)—NH-⇌-C(—OH)=N—) and amidine (—C(=NR)—NH-⇌-C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10th Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The definitions described herein may be appended to form chemically-relevant combinations, such as "heteroalkylaryl", "haloalkylheteroaryl", "arylalkylheterocyclyl", "alkylcarbonyl", "alkoxyalkyl", and the like. When the term "alkyl" is used as a suffix following another term, as in "phenylalkyl", or "hydroxyalkyl", this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

The term "spirocycloalkyl", as used herein, means a spirocyclic cycloalkyl group, such as, for example, spiro[3.3]heptane. The term spiroheterocycloalkyl, as used herein, means a spirocyclic heterocycloalkyl, such as, for example, 2,6-diaza spiro[3.3]heptane.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl refers to a group —C(=O)R contain 6 carbon atoms. The term "arylcarbonyl" as used herein means a group of formula C(=O)R wherein R is an aryl group; the term "benzoyl" as used herein an "arylcarbonyl" group wherein R is phenyl.

The term "ester" as used herein denotes a group of formula —C(=O)OR wherein R is lower alkyl as defined herein.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl", or "hydroxyalkyl", this is intended to refer to an alkyl group, as defined above, being substituted with one to two substituents selected from the other specifically-named group. Thus, for example, "phenylalkyl" denotes the radical R'R''—, wherein R' is a phenyl radical, and R'' is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical.

The terms "haloalkyl" or "halo-lower alkyl" or "lower haloalkyl" refers to a straight or branched chain hydrocarbon residue containing 1 to 6 carbon atoms wherein one or more carbon atoms are substituted with one or more halogen atoms.

The term "alkylene" or "alkylenyl" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —CH$_2$CH(i-Pr)CH$_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The term "PCy$_3$" refers to a phosphine trisubstituted with three cyclic moieties.

The terms "haloalkoxy" or "halo-lower alkoxy" or "lower haloalkoxy" refers to a lower alkoxy group, wherein one or more carbon atoms are substituted with one or more halogen atoms.

The term "hydroxyalkyl" as used herein denotes an alkyl radical as herein defined wherein one to three hydrogen atoms on different carbon atoms is/are replaced by hydroxyl groups.

The terms "alkylsulfonyl" and "arylsulfonyl" as used herein refers to a group of formula —S(=O)$_2$R wherein R is alkyl or aryl respectively and alkyl and aryl are as defined herein. The term "heteroalkylsulfonyl" as used herein refers herein denotes a group of formula —S(=O)$_2$R wherein R is "heteroalkyl" as defined herein.

The terms "alkylsulfonylamino" and "arylsulfonylamino" as used herein refers to a group of formula —NR'S(=O)$_2$R wherein R is alkyl or aryl respectively, R' is hydrogen or $C_{1-3}$ alkyl, and alkyl and aryl are as defined herein.

The term "cycloalkyl" as used herein refers to a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to a cycloalkyl composed of 3 to 7 carbons in the carbocyclic ring.

The term "carboxy-alkyl" as used herein refers to an alkyl moiety wherein one, hydrogen atom has been replaced with a carboxyl with the understanding that the point of attachment of the heteroalkyl radical is through a carbon atom. The term "carboxy" or "carboxyl" refers to a —CO$_2$H moiety.

The term "heteroaryl" or "heteroaromatic" as used herein means a monocyclic or bicyclic radical of 5 to 12 ring atoms having at least one aromatic or partially unsaturated ring containing four to eight atoms per ring, incorporating one or more N, O, or S heteroatoms, the remaining ring atoms being carbon, with the understanding that the attachment point of the heteroaryl radical will be on an aromatic or partially unsaturated ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, oxazinyl, pyrrolyl, pyrazolyl, imidazolyl, oxazolyl, 4,5-Dihydro-oxazolyl, 5,6-Dihydro-4H-[1,3]oxazolyl, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, lower haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole, naphthyridinyl, 5,6,7,8-Tetrahydro-[1,6]naphthyridinyl, and benzisothiazole. Bicyclic moieties can be optionally substituted on either ring, however the point of attachment is on a ring containing a heteroatom.

The term "heterocyclyl", "heterocycloalkyl", or "heterocycle" as used herein denotes a monovalent saturated cyclic radical, consisting of one or more rings, preferably one to two rings, including spirocyclic ring systems, of three to eight atoms per ring, incorporating one or more ring heteroatoms (chosen from N, O or $S(O)_{0-2}$), and which can optionally be independently substituted with one or more, preferably one or two substituents selected from hydroxy, oxo, cyano, lower alkyl, lower alkoxy, lower haloalkoxy, alkylthio, halo, lower haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, and ionic forms thereof, unless otherwise indicated. Examples of heterocyclic radicals include, but are not limited to, morpholinyl, piperazinyl, piperidinyl, azetidinyl, pyrrolidinyl, hexahydroazepinyl, oxetanyl, tetrahydrofuranyl, tetrahydrothiophenyl, oxazolidinyl, thiazolidinyl, isoxazolidinyl, tetrahydropyranyl, thiomorpholinyl, quinuclidinyl and imidazolinyl, and ionic forms thereof. Examples may also be bicyclic, such as, for example, 3,8-diaza-bicyclo[3.2.1]octane, 2,5-diaza-bicyclo[2.2.2]octane, or octahydro-pyrazino[2,1-c][1,4]oxazine.

Inhibitors of BTK

The application provides a compound of Formula I,

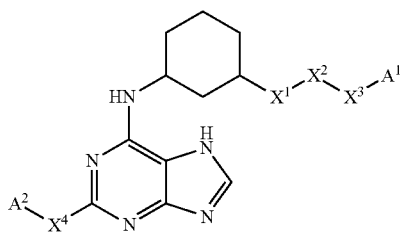

wherein:
$A^1$ is H or $A^{1'}$;
$A^{1'}$ is lower alkyl or phenyl, optionally substituted with one or more $A^{1''}$;
each $A^{1''}$ is independently halo or lower alkyl;
$A^2$ is H or $A^{2'}$;
$A^{2'}$ is heteroaryl, optionally substituted with lower alkyl;
$X^1$ is —NH, C(=O), or absent;
$X^2$ is —NH, C(=O), or absent;
$X^3$ is lower alkylene or absent; and
$X^4$ is —NH or absent;
or a pharmaceutically acceptable salt thereof.

The application provides a compound of Formula I, wherein $X^1$ is —NH.

The application provides the above compound of Formula I, wherein $X^2$ is —C(=O).

The application provides the above compound of Formula I, wherein $X^3$ is absent.

The application provides the above compound of Formula I, wherein $A^1$ is phenyl, optionally substituted with one or more $A^{1''}$.

The application provides the above compound of Formula I, wherein $X^4$ is absent.

The application provides the above compound of Formula I, wherein $A^2$ is H.

The application provides a compound of Formula I, wherein $X^1$ is —C(=O).

The application provides the above compound of Formula I, wherein $X^2$ is —NH.

The application provides the above compound of Formula I, wherein $X^3$ is methylene.

The application provides the above compound of Formula I, wherein $A^1$ is phenyl, optionally substituted with one or more $A^{1''}$.

The application provides the above compound of Formula I, wherein $A^2$ is H.

The application provides the above compound of Formula I, wherein $X^4$ is absent.

The application provides a compound of Formula I, wherein $X^4$ is —NH, $A^2$ is pyrazolyl, and $A^{2'}$ is methyl.

The application provides a compound of Formula I, selected from the group consisting of:
4-tert-butyl-N-[3-(7H-purin-6-ylamino)cyclohexyl]benzamide;
N-[(3-chlorophenyl)methyl]-3-(9H-purin-6-ylamino)cyclohexane-1-carboxamide;
6-N-cyclohexyl-2-N-(1-methylpyrazol-4-yl)-9H-purine-2,6-diamine;
6-N-(3-methylcyclohexyl)-2-N-(1-methylpyrazol-4-yl)-9H-purine-2,6-diamine; and
4-tert-butyl-N-[3-[[2-[(1-methylpyrazol-4-yl)amino]-9H-purin-6-yl]amino]cyclohexyl]benzamide.

The application provides a method for treating an inflammatory and/or autoimmune condition comprising administering to a patient in need thereof a therapeutically effective amount of the compound of Formula I.

The application provides a method for treating rheumatoid arthritis comprising administering to a patient in need thereof a therapeutically effective amount of the compound of Formula I.

The application provides a method for treating asthma comprising administering to a patient in need thereof a therapeutically effective amount of the compound of Formula I.

The application provides a pharmaceutical composition comprising the compound of Formula I.

The application provides a pharmaceutical composition comprising the compound of Formula I, admixed with at least one pharmaceutically acceptable carrier, excipient or diluent.

The application provides a use of the compound of formula I in the manufacture of a medicament for the treatment of an inflammatory disorder.

The application provides a use of the compound of formula I in the manufacture of a medicament for the treatment of an autoimmune disorder.

The application provides a use of the compound of formula I in the manufacture of a medicament for the treatment of rheumatoid arthritis.

The application provides a use of the compound of formula I in the manufacture of a medicament for the treatment of asthma.

The application provides the use of a compound as described above for the treatment of inflammatory and/or autoimmune condition.

The application provides the use of a compound as described above for the treatment of rheumatoid arthritis.

The application provides the use of a compound as described above for the treatment of asthma.

The application provides a compound, method, or composition as described herein.

Compounds and Preparation

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I depicts examples of compounds according to generic Formula I:

TABLE I

| Compound | Nomenclature | Structure |
|---|---|---|
| I-1 | 4-tert-Butyl-N-[3-(9H-purin-6-ylamino)-cyclohexyl]-benzamide | 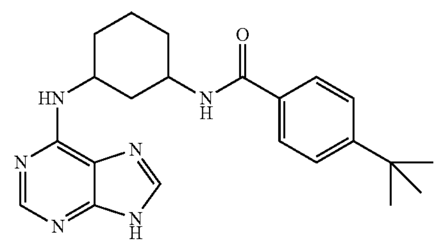 [SMILES: CC(C)(C)c1ccc(C(=O)NC2CCCC(Nc3ncnc4[nH]cnc34)C2)cc1] |
| I-2 | 3-(9H-Purin-6-ylamino)-cyclohexanecarboxylic acid 3-chloro-benzylamide | 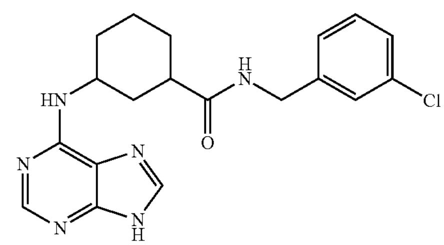 [SMILES: O=C(NCc1cccc(Cl)c1)C1CCCC(Nc2ncnc3[nH]cnc23)C1] |
| I-3 | N*6*-Cyclohexyl-N*2*-(1-methyl-1H-pyrazol-4-yl)-9H-purine-2,6-diamine | 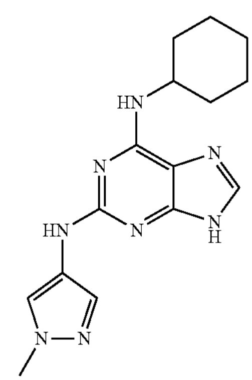 [SMILES: Cn1cc(Nc2nc(NC3CCCCC3)c3nc[nH]c3n2)cn1] |
| I-4 | N*6*-(3-Methyl-cyclohexyl)-N*2*-(1-methyl-1H-pyrazol-4-yl)-9H-purine-2,6-diamine | 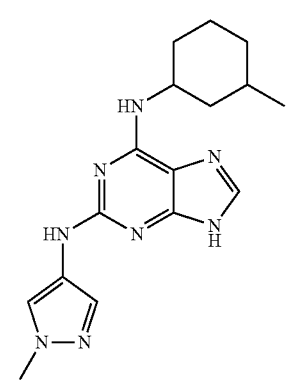 |

TABLE I-continued

| Compound | Nomenclature | Structure |
|---|---|---|
| I-5 | 4-tert-Butyl-N-{3-[2-(1-methyl-1H-pyrazol-4-ylamino)-9H-purin-6-ylamino]-cyclohexyl}-benzamide | 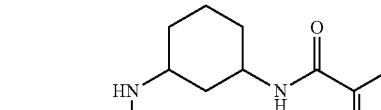 |

General Synthetic Schemes

The compounds of the present invention may be prepared by any conventional means. Suitable processes for synthesizing these compounds are provided in the examples. Generally, compounds of the invention may be prepared according to the schemes below.

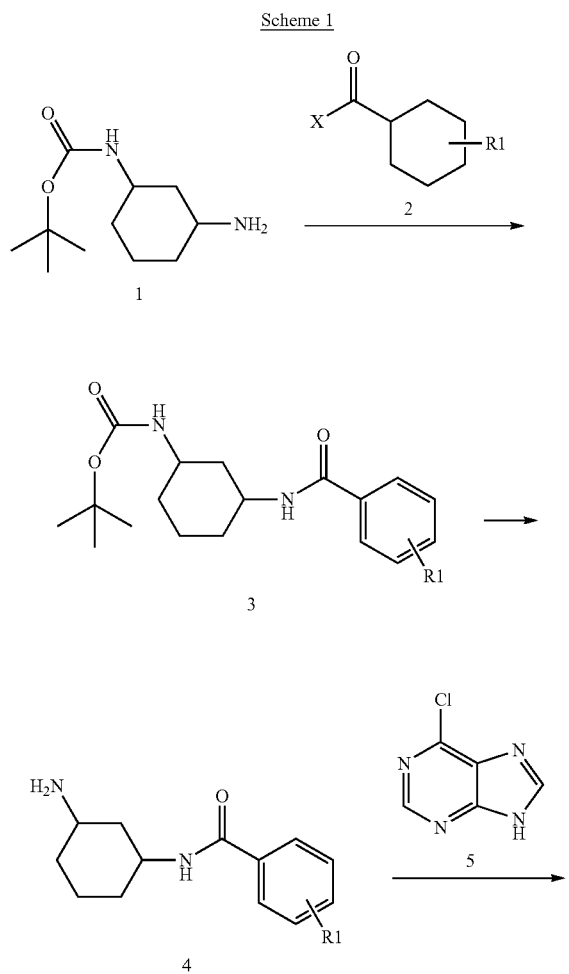

Compound of formula 6 where R1 is as described above in the genus of formula I, may be prepared according to scheme 1. Starting with (3-amino-cyclohexyl)-carbamic acid tert-butyl ester (compound 1), an acylation reaction with 2 can occur to give an amide bond in compound of formula 3. When in compound 2, X=Cl, mild base such as triethylamine and DIPEA will perform the reaction. When in compound 2, X=OH, a coupling reagent such as O-(7-azabenzotriazol-1-yl)-N,N,N',N'-tetramethyluronium hexafluoro-phosphate (HATU) in presence of a base using a polar solvent such as DMF will provide compound of formula 3. A list of coupling reagents that could also be used for this transformation can be found in this review (*Chemical Review* 2011, 111, 6557). The tert-butoxycarbonyl (BOC) protecting group could easily be removed under acidic conditions such as TFA/DCM mixture to afford free amine of formula 4. Other protecting groups could be used and would be known to those skilled in art. (For a leading reference, see P. G. M. Wuts and T. W. Greene in Green's Protective Groups in Organic Synthesis, Wiley and Sons, 2007). The free amine derivative 4 could then be coupled with 6-chloropurine 5 under microwave irradiation to provide derivative 6 through a nucleophilic aromatic substitution. More information about the use of microwave in organic synthesis is described in this review: *Current Organic Chemistry*, 2010, 14, 1050. This transformation could also be accomplished under conventional heating at temperature around 100° C. using a base such as DIPEA and a solvent such as DMF for reaction times between 3 and several hours.

Scheme 2

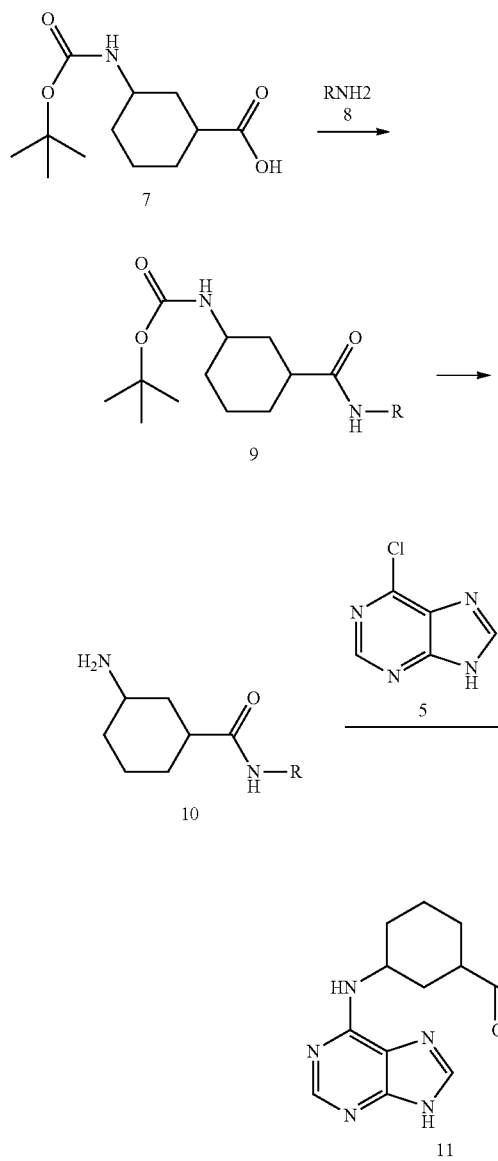

Similarly, compound of formula 11 where R is as described above in the genus of formula 1 may be prepared according to scheme 2. Starting from 3-tert-butylcarbonylamino-cyclohexanecarboxylic acid, compound 7, the same sequence described above in scheme 1 can be applied to prepare compound of formula 11.

Scheme 3

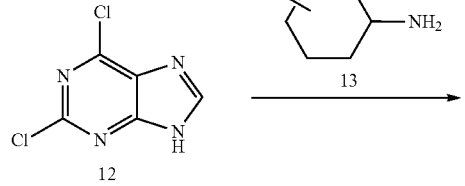

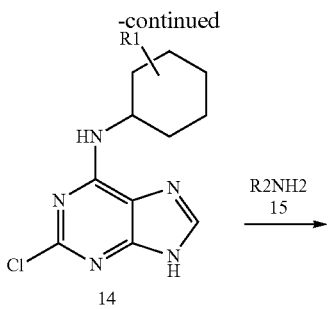

The compound of formula 16 may be prepared as shown in scheme 3. According to this procedure, 2,6-dichloro-9H-purine (12) undergoes a nucleophilic aromatic substitution. This reaction may proceeds under conventional heating at temperature around 100° C. in presence of a base such as di-isopropylethylamine and a polar solvent such as DMF for reaction times between 3 hours and several hours. Alternatively, the reaction can occur under microwave irradiation at temperature around 150° C. for reaction times between 30 minutes and 2 hours. The more reactive chlorine at the 6-position on compound 12 was regioselectively displaced during this reaction. The less reactive chlorine at the 2-position needed more harsh conditions and required the use of an excess of TMSCl and 1-methyl-1H-pyrazol-4amine heated in a microwave at 160° C. for 1 hour. (related procedure: *Organic Process Research & Development* 2006, 10, 799) to give the compound of the invention formula 16.

Scheme 4

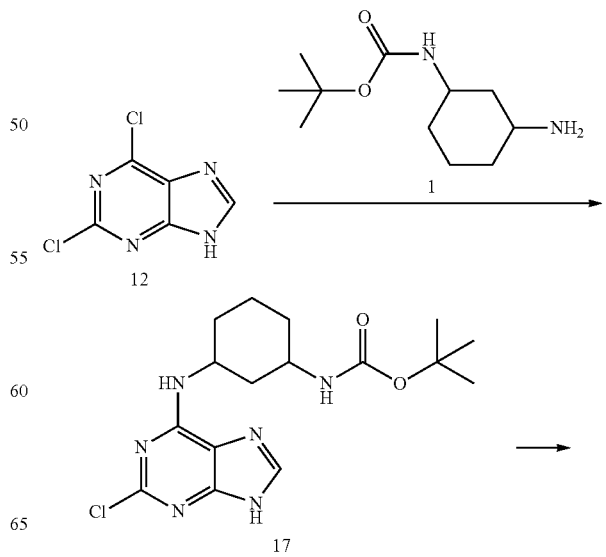

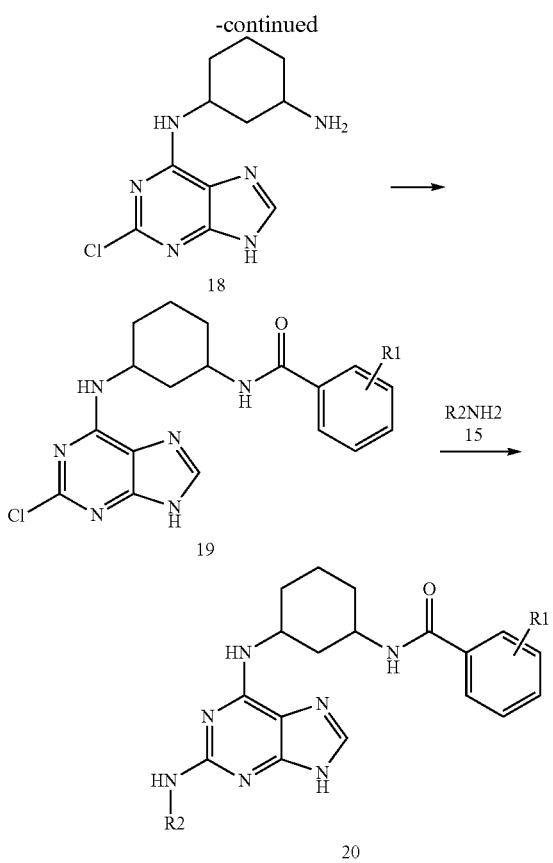

Compounds of the invention of formula 20 may be made as shown in scheme 4. Similar steps to obtain compound of formula 20 have been described above.

Pharmaceutical Compositions and Administration

The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stiffing. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Indications and Methods of Treatment

The compounds of generic Formula I inhibit Bruton's tyrosine kinase (BTK). Activation of BTK by upstream kinases results in activation of phospholipase-Cγ which, in turn, stimulates release of pro-inflammatory mediators. Compounds of Formula I are useful in the treatment of arthritis and other anti-inflammatory and auto-immune diseases. Compounds according to Formula I are, accordingly, useful for the treatment of arthritis. Compounds of Formula I are useful for inhibiting BTK in cells and for modulating B-cell development. The present invention further comprises pharmaceutical compositions containing compounds of Formula I admixed with pharmaceutically acceptable carrier, excipients or diluents.

The compounds described herein are kinase inhibitors, in particular BTK inhibitors. These inhibitors can be useful for treating one or more diseases responsive to kinase inhibition, including diseases responsive to BTK inhibition and/or inhibition of B-cell proliferation, in mammals. Without wishing to be bound to any particular theory, it is believed that the interaction of the compounds of the invention with BTK results in the inhibition of BTK activity and thus in the pharmaceutical utility of these compounds. Accordingly, the invention includes a method of treating a mammal, for instance a human, having a disease responsive to inhibition of BTK activity, and/or inhibiting B-cell proliferation, comprising administrating to the mammal having such a disease, an effective amount of at least one chemical entity provided herein. An effective concentration may be ascertained experimentally, for example by assaying blood concentration of the compound, or theoretically, by calculating bioavailability. Other kinases that may be affected in addition to BTK include, but are not limited to, other tyrosine kinases and serine/threonine kinases.

Kinases play notable roles in signaling pathways controlling fundamental cellular processes such as proliferation, differentiation, and death (apoptosis). Abnormal kinase activity has been implicated in a wide range of diseases, including multiple cancers, autoimmune and/or inflammatory diseases, and acute inflammatory reactions. The multifaceted role of kinases in key cell signaling pathways provides a significant opportunity to identify novel drugs targeting kinases and signaling pathways.

An embodiment includes a method of treating a patient having an autoimmune and/or inflammatory disease, or an acute inflammatory reaction responsive to inhibition of BTK activity and/or B-cell proliferation.

Autoimmune and/or inflammatory diseases that can be affected using compounds and compositions according to the invention include, but are not limited to: psoriasis, allergy, Crohn's disease, irritable bowel syndrome, Sjogren's disease, tissue graft rejection, and hyperacute rejection of transplanted organs, asthma, systemic lupus erythematosus (and associated glomerulonephritis), dermatomyositis, multiple sclerosis, scleroderma, vasculitis (ANCA-associated and other vasculitides), autoimmune hemolytic and thrombocytopenic states, Goodpasture's syndrome (and associated glomerulonephritis and pulmonary hemorrhage), atherosclerosis, rheumatoid arthritis, chronic Idiopathic thrombocytopenic purpura (ITP), Addison's disease, Parkinson's disease, Alzheimer's disease, diabetes, septic shock, and myasthenia gravis.

Included herein are methods of treatment in which at least one chemical entity provided herein is administered in combination with an anti-inflammatory agent. Anti-inflammatory agents include but are not limited to NSAIDs, non-specific and COX-2 specific cyclooxgenase enzyme inhibitors, gold compounds, corticosteroids, methotrexate, tumor necrosis factor receptor (TNF) receptors antagonists, immunosuppressants and methotrexate.

Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib and/or etoricoxib.

In some embodiments, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory compound is an anti-C5 monoclonal antibody (such as eculizumab or pexelizumab), a TNF antagonist, such as entanercept, or infliximab, which is an anti-TNF alpha monoclonal antibody.

Still other embodiments of the invention pertain to combinations in which at least one active agent is an immunosuppressant compound such as an immunosuppressant compound chosen from methotrexate, leflunomide, cyclosporine, tacrolimus, azathioprine, and mycophenolate mofetil.

B-cells and B-cell precursors expressing BTK have been implicated in the pathology of B-cell malignancies, including, but not limited to, B-cell lymphoma, lymphoma (including Hodgkin's and non-Hodgkin's lymphoma), hairy cell lymphoma, multiple myeloma, chronic and acute myelogenous leukemia and chronic and acute lymphocytic leukemia.

BTK has been shown to be an inhibitor of the Fas/APO-1 (CD-95) death inducing signaling complex (DISC) in B-lineage lymphoid cells. The fate of leukemia/lymphoma cells may reside in the balance between the opposing proapoptotic effects of caspases activated by DISC and an upstream anti-apoptotic regulatory mechanism involving BTK and/or its substrates (Vassilev et al., *J. Biol. Chem.* 1998, 274, 1646-1656).

It has also been discovered that BTK inhibitors are useful as chemosensitizing agents, and, thus, are useful in combination with other chemotherapeutic drugs, in particular, drugs that induce apoptosis. Examples of other chemotherapeutic drugs that can be used in combination with chemosensitizing BTK inhibitors include topoisomerase I inhibitors (camptothecin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines).

BTK activity has also be associated with some leukemias expressing the bcr-abl fusion gene resulting from translocation of parts of chromosome 9 and 22. This abnormality is commonly observed in chronic myelogenous leukemia. BTK is constitutively phosphorylated by the bcr-abl kinase which initiates downstream survival signals which circumvents apoptosis in bcr-abl cells. (N. Feldhahn et al. *J. Exp. Med.* 2005 201(11): 1837-1852).

Methods of Treatment

The application provides a method for treating an inflammatory and/or autoimmune condition comprising administering to a patient in need thereof a therapeutically effective amount of the compound of Formula I.

The application provides a method for treating an inflammatory condition comprising administering to a patient in need thereof a therapeutically effective amount of the compound of Formula I.

The application provides a method for treating rheumatoid arthritis comprising administering to a patient in need thereof a therapeutically effective amount of the compound of Formula I.

The application provides a method for treating asthma comprising administering to a patient in need thereof a therapeutically effective amount of Formula I.

The application provides a method for treating an inflammatory and/or autoimmune condition comprising administering to a patient in need thereof a therapeutically effective amount of the BTK inhibitor compound of Formulae I.

The application provides a method for treating arthritis comprising administering to a patient in need thereof a therapeutically effective amount of the BTK inhibitor compound of Formula I.

The application provides a method for treating asthma comprising administering to a patient in need thereof a therapeutically effective amount of the BTK inhibitor compound of Formula I.

The application provides a method of inhibiting B-cell proliferation comprising administering to a patient in need thereof a therapeutically effective amount of the BTK inhibitor compound of Formula I.

The application provides a method for inhibiting BTK activity comprising administering the BTK inhibitor compound of any one of Formula I, wherein the BTK inhibitor compound exhibits an $IC_{50}$ of 50 micromolar or less in an in vitro biochemical assay of BTK activity.

In one variation of the above method, the BTK inhibitor compound exhibits an $IC_{50}$ of 100 nanomolar or less in an in vitro biochemical assay of BTK activity.

In another variation of the above method, the compound exhibits an $IC_{50}$ of 10 nanomolar or less in an in vitro biochemical assay of BTK activity.

The application provides a method for treating an inflammatory condition comprising co-administering to a patient in need thereof a therapeutically effective amount of an anti-inflammatory compound in combination with the BTK inhibitor compound of Formula I.

The application provides a method for treating arthritis comprising co-administering to a patient in need thereof a therapeutically effective amount of an anti-inflammatory compound in combination with the BTK inhibitor compound of Formula I.

The application provides a method for treating a lymphoma or a BCR-ABL1+ leukemia cells by administering to a patient in need thereof a therapeutically effective amount of the BTK inhibitor compound of Formula I.

The invention provides the use of a compound as described above as therapeutically active substance.

The invention provides the use of a compound as described above in the treatment of an inflammatory and/or autoimmune condition.

The invention provides the use of a compound as described above for the preparation of a medicament for the treatment of an inflammatory and/or autoimmune condition.

The invention provides a compound as described above for use in the treatment of an inflammatory and/or autoimmune condition.

The invention provides a compound as described above for use in the treatment of rheumatoid arthritis.

The invention provides a compound as described above for use in the treatment of asthma.

The invention provides the invention as hereinbefore described.

EXAMPLES

Abbreviations

AcOH acetic acid
BOC tert-butoxycarbonyl

Bu butyl
BuOH butanol
CDI carbonyldiimidazole
$Cs_2CO_3$ cesium carbonate
DCM dichloromethane
DHP dihydropyran
DMA dimethylacetamide
DIPEA diisopropylethylamine
DMF N,N-dimethylformamide
DMSO dimethylsulfoxide
EtOAc ethyl acetate
EtOH ethyl alcohol
H hour
HATU O-(7-azabenzotriazol-1-yl)-N,N,N',N'-tetramethyluronium hexafluorophosphate
HCl Hydrogen chloride
LC-MS Liquid Chromatography Mass Spectrometry
HPLC high pressure liquid chromatography
$K_2CO_3$ potassium carbonate
MeOH methyl alcohol
Min minutes
MW microwave
NMP 1-methyl-2-pyrrolidinone
Pd/C palladium on charcoal
$PdCl_2$(dppf) [1,1'-Bis(diphenylphosphino)ferrocene]dichloropalladium(II)
$Pd_2$(dba)$_3$ tris(dibenzylideneacetone)dipalladium(0)
Pd(OAc)$_2$ palladium(II) acetate
Pd(PPh$_3$)$_4$ palladium tetrakistriphenylphosphine
PTSA para-toluene sulfonic acid
RT (or rt) room temperature
tBuOK potassium tert-butoxide
TFA trifluoroacetic acid
THF tetrahydrofuran
THP tetrahydropyran
TLC thin layer chromatography
TMSCl trimethylsilyl chloride
Xphos 2-dicyclohexylphosphino-2',4',6'-triisopropylbiphenyl Commonly used abbreviations include: acetyl (Ac), azobis-isobutyrylnitrile (AIBN), atmospheres (Atm), 9-borabicyclo[3.3.1]nonane (9-BBN or BBN), 2,2'-bis(diphenylphosphino)-1,1'-binaphthyl (BINAP), tert-butoxycarbonyl (Boc), di-tert-butyl pyrocarbonate or boc anhydride (BOC$_2$O), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), 2,3-Dichloro-5,6-dicyano-1,4-benzoquinone (DDQ), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), 2-ethoxy-1-ethoxycarbonyl-1,2-dihydroquinoline (EEDQ), ethyl (Et), ethyl acetate (EtOAc), ethanol (EtOH), 2-ethoxy-2H-quinoline-1-carboxylic acid ethyl ester (EEDQ), diethyl ether (Et$_2$O), ethyl isopropyl ether (EtOiPr), O-(7-azabenzotriazole-1-yl)-N, N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), isopropylmagnesium chloride (iPrMgCl), hexamethyl disilazane (HMDS), liquid chromatography mass spectrometry (LCMS), lithium hexamethyl disilazane (LiHMDS), meta-chloroperoxybenzoic acid (m-CPBA), methanol (MeOH), melting point (mp), MeSO$_2$— (mesyl or Ms), methyl (Me), acetonitrile (MeCN), m-chloroperbenzoic acid (MCPBA), mass spectrum (ms), methyl t-butyl ether (MTBE), methyl tetrahydrofuran (MeTHF), N-bromosuccinimide (NBS), n-Butyllithium (nBuLi), N-carboxyanhydride (NCA), N-chlorosuccinimide (NCS), N-methylmorpholine (NMM), N-methylpyrrolidone (NMP), pyridinium chlorochromate (PCC), Dichloro-((bis-diphenylphosphino)ferrocenyl) palladium(II) (Pd(dppf)Cl$_2$), palladium(II) acetate (Pd(OAc)$_2$), tris(dibenzylideneacetone)dipalladium(0) (Pd$_2$(dba)$_3$), pyridinium dichromate (PDC), phenyl (Ph), propyl (Pr), iso-propyl (i-Pr), pounds per square inch (psi), pyridine (pyr), 1,2,3,4,5-Pentaphenyl-1'-(di-tert-butylphosphino)ferrocene (Q-Phos), room temperature (ambient temperature, rt or RT), sec-Butyllithium (sBuLi), tert-butyldimethylsilyl or t-BuMe$_2$Si (TBDMS), tetra-n-butylammonium fluoride (TBAF), triethylamine (TEA or Et$_3$N), 2,2,6,6-tetramethylpiperidine 1-oxyl (TEMPO), trimethylsilylethoxymethyl (SEM), triflate or CF$_3$SO$_2$-(TO, trifluoroacetic acid (TFA), 1,1'-bis-2,2,6,6-tetramethylheptane-2,6-dione (TMHD), 0-benzotriazol-1-yl-N,N,N',N'-tetramethyluronium tetrafluoroborate (TBTU), thin layer chromatography (TLC), tetrahydrofuran (THF), trimethylsilyl or Me$_3$Si (TMS), p-toluenesulfonic acid monohydrate (TsOH or pTsOH), 4-Me-C$_6$H$_4$SO$_2$— or tosyl (Ts), and N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

General Conditions

Compounds of the present invention can be prepared beginning with the commercially available starting materials by utilizing general synthetic techniques and procedures known to those skilled in the art. Outlines below are reaction schemes suitable for preparing such compounds. Further exemplification can be found in the specific examples.

Preparative Examples

Reagents were purchased from Aldrich, Sigma, Maybridge, Oakwood, Arkpharminc or other suppliers and used without further purification. Reactions using microwave irradiation for heating were conducted using either a Personal Chemistry Emrys Optimizer System or a CEM Discovery System. The purification of multi-milligram to multi-gram scale compounds was conducted by methods known know to those skilled in the art such as of silica gel flash chromatography; preparative flash column purifications were also effected in some cases by use of disposal pre-packed multigram silica gel columns (RediSep)™ eluted with a CombiFlash system. Biotage™ and ISCO™ are also flash column instruments that may have been used in this invention for purification of intermediates.

For the purpose of judging compound identity and purity, LC/MS (liquid chromatography/mass spectroscopy) spectra were recorded using the following system. For measurement of mass spectra, the system consists of a Micromass Platform II spectrometer: ES Ionization in positive mode (mass range: 150-1200 amu). The simultaneous chromatographic separation was achieved with the following HPLC system: ES Industries Chromegabond WR C-18 3u 120 Å (3.2×30 mm) column cartridge; Mobile Phase A: Water (0.02% TFA) and Phase B: Acetonitrile (0.02% TFA); gradient 10% B to 90% B in 3 minutes; equilibration time of 1 minute; flow rate of 2 mL/minute.

Many compounds of Formula 1 were also purified by reversed phased HPLC, using methods well known to those skilled in the art. In some cases, preparative HPLC purification was conducted using PE Sciex 150 EX Mass Spec controlling a Gilson 215 collector attached to a Shimadzu preparative HPLC system and a Leap autoinjector. Compounds were collected from the elution stream using LC/MS detection in the positive ion detection: The elution of compounds from C-18 columns (2.0×10 cm eluting at 20 ml/min) was effected using appropriate linear gradation mode over 10 minutes of Solvent (A) 0.05% TFA/H2O and Solvent (B) 0.035% TFA/acetonitrile. For injection on to HPLC systems, the crude samples were dissolved in mixtures of methanol, acetonitrile and DMSO. Compounds were characterized either by $^1$H-NMR using a Bruker 400 MHz NMR Spectrometer.

The compounds of the present invention may be synthesized according to known techniques. The following examples and references are provided to aid the understanding of the present invention. The examples are not intended, however, to limit the invention, the true scope of which is set forth in the appended claims. The names of the final products in the examples were generated using Isis AutoNom 2000.

Example 1

4-tert-Butyl-N-[3-(7H-purin-6-ylamino)-cyclohexyl]-benzamide

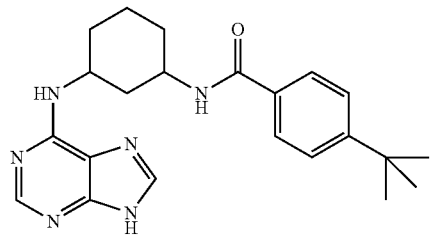 [SMILES: CC(C)(C)c1ccc(C(=O)NC2CCCC(Nc3ncnc4[nH]cnc34)C2)cc1]

Step 1) [3-(4-tert-butyl-benzoylamino)-cyclohexyl]-carbamic acid tert-butyl ester

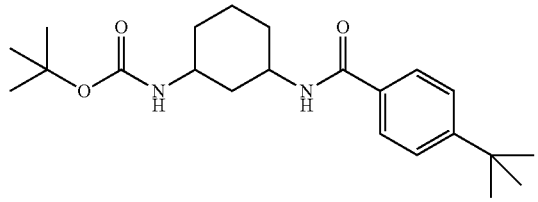 [SMILES: CC(C)(C)OC(=O)NC1CCCC(NC(=O)c2ccc(C(C)(C)C)cc2)C1]

To a stirred solution of (3-amino-cyclohexyl)-carbamic acid tert-butyl ester (0.250 g, 1.16 mmol) in DMF (10.0 mL) was added diisopropylethylamine (1.5 mL, 7 mmol) at RT. After 15 min of stirring at the same temperature, HATU (0.529 g, 1.39 mmol) was added into the reaction mixture followed by the addition of 4-tert-butyl-benzoic acid (0.208 g, 1.16 mmol). The reaction mixture was stirred at room temperature for 16 hours. After dilution with water (10 mL), the mixture was extracted with ethyl acetate (2×50 mL). The combined organic phases were washed with water, brine and dried over anhydrous sodium sulfate. The solvent was removed under reduced pressure. The crude material was purified by column chromatography (silica gel, 10% ethyl acetate-hexane) to give [3-(4-tert-butyl-benzoylamino)-cyclohexyl]-carbamic acid tert-butyl ester (0.250 g, 48%) as white solid. LC/MS: m/z calculated for $C_{22}H_{34}N_2O_3$ ([M+H]$^+$): 375 Found: 375.4.

Step 2) N-(3-amino-cyclohexyl)-4-tert-butyl-benzamide

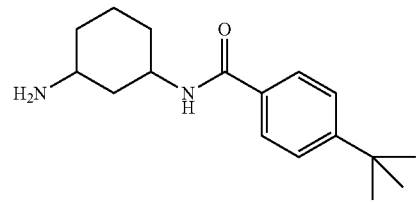 [SMILES: CC(C)(C)c1ccc(C(=O)NC2CCCC(N)C2)cc1]

To a stirred solution of [3-(4-tert-butyl-benzoylamino)-cyclohexyl]-carbamic acid tert-butyl ester (0.250 g, 0.66 mmol) in dichloromethane (8.0 mL) was added TFA (0.25 mL 3.3 mmol) at 0° C. After stirring for 15 min at 0° C., the reaction mixture was stirred at RT for 4 h. The solvent was removed under reduced pressure. The crude material was neutralized with saturated aqueous NaHCO$_3$ solution and extracted with dichloromethane (3×30 mL). The combined organic layers were dried over anhydrous sodium sulfate. The solvent was removed under reduced pressure to give N-(3-amino-cyclohexyl)-4-tert-butyl-benzamide (0.170 g, 94%) as light yellow solid. LC/MS: m/z calculated for $C_{17}H_{26}N_2O_3$ ([M+H]$^+$): 275 Found: 275.4.

Step 3) 4-tert-Butyl-N-[3-(7H-purin-6-ylamino)-cyclohexyl]-benzamide

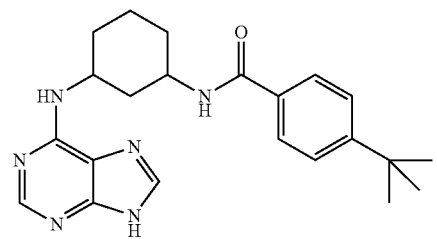

To solution of 6-chloro-9H-purine (0.100 g, 0.64 mmol) in NMP (2.0 mL) were added N-(3-amino-cyclohexyl)-4-tert-butyl-benzamide (0.211 g, 0.77 mmol) and diisopropylethylamine (0.26 mL, 1.60 mmol at RT. The reaction mixture was irradiated at 150° C. for 30 min in a microwave. The reaction mixture was diluted with water (10 mL) and extracted with ethyl acetate (2×20 mL). The combined organic phases were dried over anhydrous sodium sulfate and the solvent was removed under reduced pressure. The crude material was purified by column chromatography (silica gel, 10% MeOH-dichloromethane) to give 4-tertbutyl-N-[3-(7H-purin-6-ylamino)-cyclohexyl]-benzamide (0.037 g, 15%) as white solid. LC/MS: m/z calculated for $C_{22}H_{28}N_6O$ ([M+H]$^+$): 393 Found: 393.4.

Example 2

3-(9H-Purin-6-ylamino)-cyclohexanecarboxylic acid 3-chloro-benzylamide

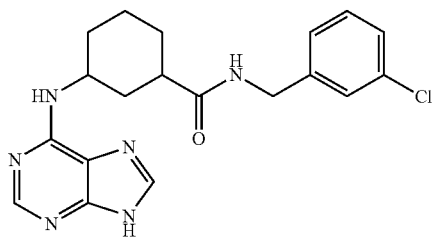 [SMILES: O=C(NCc1cccc(Cl)c1)C1CCCC(Nc2ncnc3[nH]cnc23)C1]

Step 1)
[3-(3-Chloro-benzylcarbamoyl)-cyclohexyl]-carbamic acid tert-butyl ester

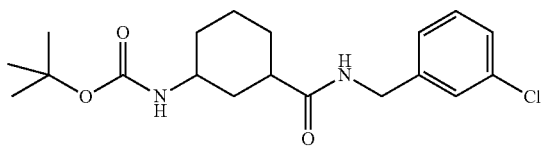 [SMILES: CC(C)(C)OC(=O)NC1CCCC(C(=O)NCc2cccc(Cl)c2)C1]

In a 250 mL round-bottomed flask, 3-(tert-butoxycarbonylamino)cyclohexanecarboxylic acid (2 g, 8.22 mmol), (3-chlorophenyl)methanamine (1.28 g, 9.04 mmol) and HATU (3.44 g, 9.04 mmol) were combined with DMF (20 mL). DIPEA (1.44 mL, 8.22 mmol) was added. The reaction mixture was stirred at room temperature for 16 hours. The reaction mixture was diluted with EtOAc and washed with water. The combined organic phases were dried over anhydrous sodium sulfate. The solvent was removed under reduced pressure. The crude material was triturated with DCM to give the desired compound which was filtered and dried under air. [3-(3-Chloro-benzylcarbamoyl)-cyclohexyl]-carbamic acid tert-butyl ester was obtained (2.8 g, 93%) as a white solid.

Step 2)
3-(9H-Purin-6-ylamino)-cyclohexanecarboxylic acid 3-chloro-benzylamide

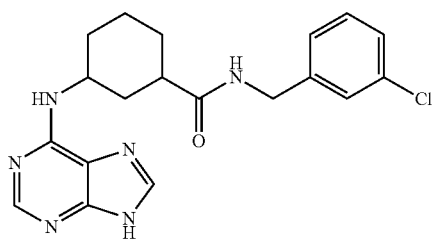 [SMILES: O=C(NCc1cccc(Cl)c1)C1CCCC(Nc2ncnc3[nH]cnc23)C1]

In a 20 mL scintillation vial, [3-(3-Chloro-benzylcarbamoyl)-cyclohexyl]-carbamic acid tert-butyl ester (1.0 g, 2.73 mmol) was dissolved with DCM (5 mL) and TFA (5 mL). The reaction mixture was stirred at room temperature for 1 hour. The solvent was removed under reduced pressure. The crude material was dissolved in DMF (2 mL). 6-chloro-9H-purine (0.463 g, 3.0 mmol) and DIPEA (2.4 mL, 13.6 mmol) were added. The reaction mixture was heated at 100° C. for 16 hours. The reaction mixture was cooled down, diluted with EtOAc and washed with water. The combined organic phases were dried over anhydrous sodium sulfate and the solvent was removed under reduced pressure. The crude material obtained was triturated with MeOH to give 3-(9H-Purin-6-ylamino)-cyclohexanecarboxylic acid 3-chloro-benzylamide (0.12 g, 11%) as a brown solid. LC/MS: m/z calculated for $C_{19}H_{21}ClN_6O$ ([M+H]$^+$): 385 Found: 385.0.

Example 3

N*6*-Cyclohexyl-N*2*-(1-methyl-1H-pyrazol-4-yl)-9H-purine-2,6-diamine

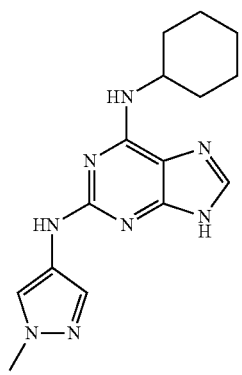

Step 1) (2-Chloro-9H-purin-6-yl)-cyclohexyl-amine

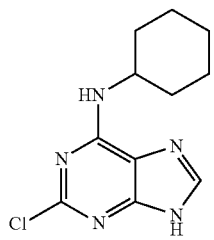 [SMILES: Clc1nc(NC2CCCCC2)c2nc[nH]c2n1]

To a solution of 2,6-dichloro-9H-purine (500 mg, 2.6 mmol) and cyclohexylamine (289 mg, 2.91 mmol) in DMF (5 mL), DIPEA (0.49 mL, 2.91 mmol) was added and heated to 100° C. for 16 h under a nitrogen atmosphere. The reaction mixture was cooled to RT and water was added. The precipitated solid was filtered, dried to give (2-chloro-9H-purin-6-yl)-cyclohexyl-amine (600 mg, 90.1%) as yellow solid. LC/MS: m/z calculated for $C_{11}H_{14}ClN_5$ ([M+H]$^+$): 252 Found: 252.

Step 2) N*6*-Cyclohexyl-N*2*-(1-methyl-1H-pyrazol-4-yl)-9H-purine-2,6-diamine

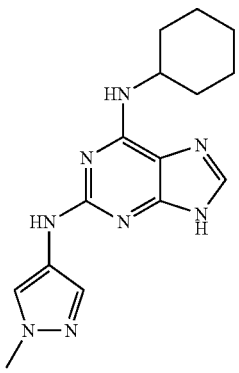 [SMILES: Cn1cc(Nc2nc(NC3CCCCC3)c3nc[nH]c3n2)cn1]

To a solution of (2-chloro-9H-purin-6-yl)-cyclohexylamine (300 mg, 1.19 mmol) in n-BuOH (2.0 mL), 1-methyl-1H-pyrazol-4-ylamine (810 mg, 8.34 mmol) and TMS-Cl (0.567 mL, 4.65 mmol) were added. The reaction mixture was irradiated at 160° C. for 1 h in a microwave. The solvent was removed under reduced pressure. The crude material was purified by preparative HPLC [Column=Gemini NX C18 (100×30 0 mm) 5µ, 5 mM NH$_4$OAc/acetonitrile] to give N*6*-cyclohexyl-N*2*-(1-methyl-1H-pyrazol-4-yl)-9H-purine-2,6-diamine (60 mg, 16%) as off white solid. LC/MS: m/z calculated for C$_{15}$H$_{20}$N$_8$ ([M+H]$^+$): 313 Found: 313.2.

Example 4

N*6*-(3-Methyl-cyclohexyl)-N*2*-(1-methyl-1H-pyrazol-4-yl)-9H-purine-2,6-diamine

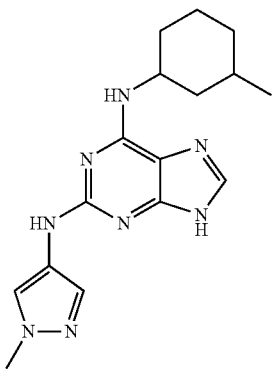

Step 1) (2-Chloro-9H-purin-6-yl)-(3-methyl-cyclohexyl)-amine

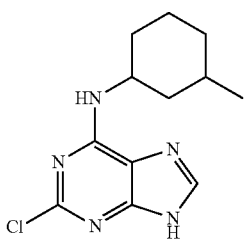 [SMILES: CC1CCCC(Nc2nc(Cl)nc3[nH]cnc23)C1]

To a solution of 2,6-dichloro-9H-purine (500 mg, 2.6 mmol) and 3-methyl-cyclohexylamine (329 mg, 2.91 mmol) in DMF (5 mL), DIPEA (0.49 mL, 2.91 mmol) was added and heated to 100° C. for 16 h under a nitrogen atmosphere. The reaction mixture was cooled to RT and water was added. The precipitated solid was filtered, dried to give (2-chloro-9H-purin-6-yl)-(3-methyl-cyclohexyl)-amine (600 mg, 86%) as yellow solid. LC/MS: m/z calculated for C$_{12}$H$_{16}$ClN$_5$ ([M+H]$^+$): 266 Found: 266.3.

Step 2) N*6*-(3-Methyl-cyclohexyl)-N*2*-(1-methyl-1H-pyrazol-4-yl)-9H-purine-2,6-diamine

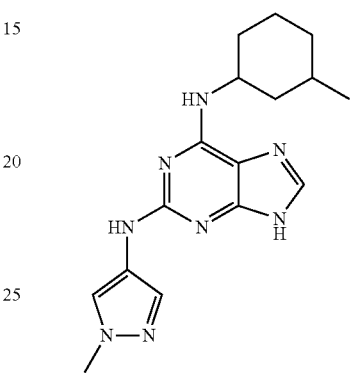

To a solution of (2-chloro-9H-purin-6-yl)-(3-methyl-cyclohexyl)-amine (200 mg, 0.755 mmol) in n-BuOH (2.0 mL), 1-methyl-1H-pyrazol-4-ylamine (513 mg, 5.3 mmol) and TMS-Cl (0.36 mL, 2.94 mmol) were added. The reaction mixture was irradiated at 160° C. for 1 h in a microwave. The solvent was removed under reduced pressure. The crude material was purified by preparative HPLC [Column=Gemini NX C18 (100×30.0 mm) 5µ, 5 mM NH$_4$OAc/acetonitrile] to give N*6*-(3-Methyl-cyclohexyl)-N*2*-(1-methyl-1H-pyrazol-4-yl)-9H-purine-2,6-diamine (65 mg, 27%) as off white solid. LC/MS: m/z calculated for C$_{16}$H$_{22}$N$_8$ ([M+H]$^+$): 327 Found: 327.2.

Example 5

4-tert-butyl-N-{3-[2-(1-methyl-1H-pyrazol-4-ylamino)-9H-purin-6-ylamino]-cyclohexyl}-benzamide

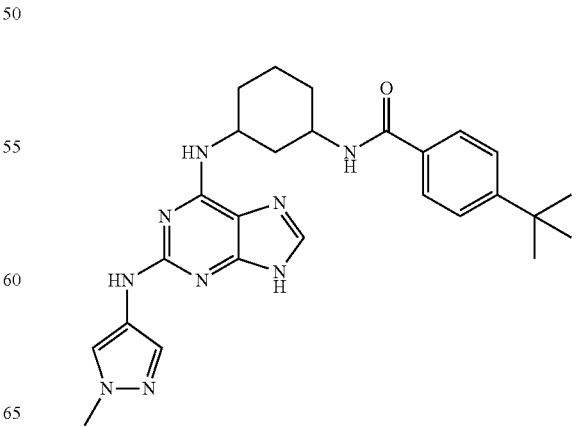

Step 1) [3-(2-Chloro-9H-purin-6-ylamino)-cyclohexyl]-carbamic acid tert-butyl ester

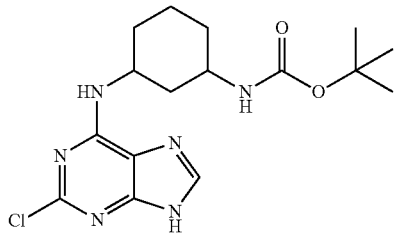 [SMILES: CC(C)(C)OC(=O)NC1CCCC(Nc2nc(Cl)nc3[nH]cnc23)C1]

To a solution of 2,6-dichloro-9H-purine (1.5 g, 7.93 mmol) and (3-amino-cyclohexyl)-carbamic acid tert-butyl ester (1.88 g, 8.73 mmol) in DMF (15 mL), DIPEA (1.49 mL, 8.73 mmol) was added and heated to 110° C. for 16 h. The reaction mixture was cooled to RT and water was added. The precipitated solid was filtered, dried to give [3-(2-chloro-9H-purin-6-ylamino)-cyclohexyl]-carbamic acid tert-butyl ester (1.8 g, crude) as brown solid. LC/MS: m/z calculated for $C_{16}H_{23}ClN_6O_2$ ([M+H]$^+$): 367 Found: 367.2.

Step 2) N-(2-Chloro-9H-purin-6-yl)-cyclohexane-1,3-diamine TFA salt

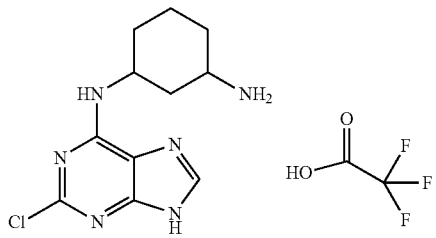 [SMILES: NC1CCCC(Nc2nc(Cl)nc3[nH]cnc23)C1 ; O=C(O)C(F)(F)F]

To a stirred solution of [3-(2-chloro-9H-purin-6-ylamino)-cyclohexyl]-carbamic acid tert-butyl ester crude (900 mg, 2.45 mmol) in DCM (5 mL) was added 33% TFA in DCM (10 mL) drop wise at 0° C. and stirred at RT for 2 h. The solvent was removed under reduced pressure. The crude material was washed with ether (2×5 mL) to give N-(2-chloro-9H-purin-6-yl)-cyclohexane-1,3-diamine as TFA salt (1.95 g, crude) as black sticky solid. LC/MS: m/z calculated for $C_{11}H_{15}ClN_6$ ([M+H]$^+$): 267 Found: 267.2.

Step 3) 4-tert-butyl-N-[3-(2-chloro-9H-purin-6-ylamino)-cyclohexyl]-benzamide

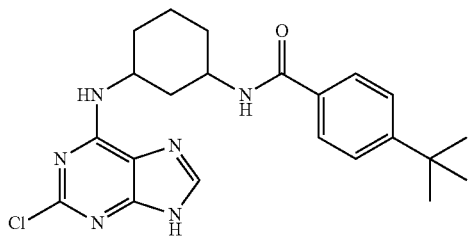 [SMILES: CC(C)(C)c1ccc(C(=O)NC2CCCC(Nc3nc(Cl)nc4[nH]cnc34)C2)cc1]

To a solution of N-(2-chloro-9H-purin-6-yl)-cyclohexane-1,3-diamine TFA salt (1.9 g, 5.0 mmol) in DMF (20 mL) was added DIPEA (2.65 mL, 15.0 mmol). The reaction mixture was stirred at RT for 15 min followed by the addition of HATU (2.28 g, 6.0 mmol) and 4-tert-butyl-benzoic acid (0.89 g, 5.0 mmol). The reaction mixture was stirred at RT for 16 h. The reaction mixture was diluted with water (40 mL) and extracted with EtOAc (2×60 mL). The combined organic layers were dried over anhydrous sodium sulfate and the solvent was removed under reduced pressure. The crude material was washed with hexane (40 mL) and dried to give 4-tert-butyl-N-[3-(2-chloro-9H-purin-6-ylamino)-cyclohexyl]-benzamide (800 mg, 47% over 3 steps) as brown solid. LC/MS: m/z calculated for $C_{22}H_{27}ClN_6O$ ([M+H]$^+$): 427 Found: 427.2.

Step 4) 4-tert-butyl-N-{3-[2-(1-methyl-1H-pyrazol-4-ylamino)-9H-purin-6-ylamino]-cyclohexyl}-benzamide

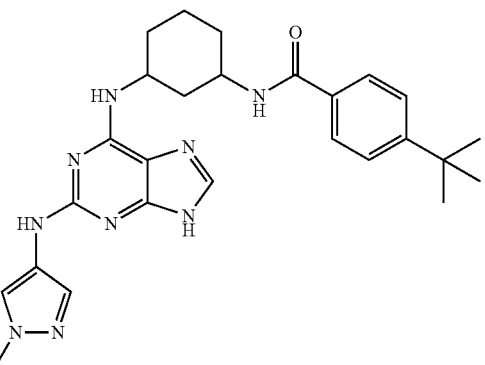

To a solution of 4-tert-butyl-N-[3-(2-chloro-9H-purin-6-ylamino)-cyclohexyl]-benzamide (200 mg, 0.46 mmol) in n-BuOH (2.0 mL), 1-methyl-1H-pyrazol-4-ylamine (319 mg, 3.28 mmol) and TMS-Cl (0.23 mL, 21.83 mmol) were added. The reaction mixture was irradiated at 160° C. for 1 h in a microwave. The solvent was removed under reduced pressure. The crude material was purified by preparative HPLC [Column=Gemini NX 110A C18 (100×30 0 mm) 5μ, 5 mM NH$_4$OAc/acetonitrile] to 4-tert-butyl-N-{3-[2-(1-methyl-1H-pyrazol-4-ylamino)-9H-purin-6-ylamino]-cyclohexyl}-benzamide (52 mg, 22%) as off white solid. LC/MS: m/z calculated for $C_{26}H_{33}N_9O$ ([M+H]$^+$): 488 Found: 488.2.

Biological Examples

Bruton's Tyrosine Kinase (BTK) Inhibition Assay

The assay is a capture of radioactive $^{33}P$ phosphorylated product through filtration. The interactions of BTK, biotinylated SH$_2$ peptide substrate (Src homology), and ATP lead to phosphorylation of the peptide substrate. Biotinylated product is bound streptavidin sepharose beads. All bound, radiolabeled products are detected by scintillation counter.

Plates assayed are 96-well polypropylene (Greiner) and 96-well 1.2 μm hydrophilic PVDF filter plates (Millipore). Concentrations reported here are final assay concentrations: 10-100 μM compounds in DMSO (Burdick and Jackson), 5-10 nM BTK enzyme (His-tagged, full-length), 30 μM peptide substrate (Biotin-Aca-AAAEEIYGEI-NH$_2$), 100

μM ATP (Sigma), 8 mM imidazole (Sigma, pH 7.2), 8 mM glycerol-2-phosphate (Sigma), 200 μM EGTA (Roche Diagnostics), 1 mM MnCl$_2$ (Sigma), 20 mM MgCl$_2$ (Sigma), 0.1 mg/ml BSA (Sigma), 2 mM DTT (Sigma), 1 μCi $^{33}$P ATP (Amersham), 20% streptavidin sepharose beads (Amersham), 50 mM EDTA (Gibco), 2 M NaCl (Gibco), 2 M NaCl w/1% phosphoric acid (Gibco), microscint-20 (Perkin Elmer).

IC$_{50}$ determinations are calculated from 10 data points per compound utilizing data produced from a standard 96-well plate assay template. One control compound and seven unknown inhibitors were tested on each plate and each plate was run twice. Typically, compounds were diluted in half-log starting at 100 μM and ending at 3 nM. The control compound was staurosporine. Background was counted in the absence of peptide substrate. Total activity was determined in the presence of peptide substrate. The following protocol was used to determine BTK inhibition.

1) Sample preparation: The test compounds were diluted at half-log increments in assay buffer (imidazole, glycerol-2-phosphate, EGTA, MnCl$_2$, MgCl$_2$, BSA).
2) Bead preparation
   a.) rinse beads by centrifuging at 500 g
   b.) reconstitute the beads with PBS and EDTA to produce a 20% bead slurry
3) Pre-incubate reaction mix without substrate (assay buffer, DTT, ATP, $^{33}$P ATP) and mix with substrate (assay buffer, DTT, ATP, $^{33}$P ATP, peptide substrate) 30° C. for 15 min
4) To start assay, pre-incubate 10 μL BTK in enzyme buffer (imidazole, glycerol-2-phosphate, BSA) and 10 μL of test compounds for 10 min at RT.
5) Add 30 μL reaction mixture without or with substrate to BTK and compounds.
6) Incubate 50 μL total assay mix for 30 min at 30° C.
7) Transfer 40 μL of assay to 150 μL bead slurry in filter plate to stop reaction.
8) Wash filter plate after 30 min, with following steps
   a. 3×250 μL NaCl
   b. 3×250 μL NaCl containing 1% phosphoric acid
   c. 1×250 μL H$_2$O
9) Dry plate for 1 h at 65° C. or overnight at RT
10) Add 50 μL microscint-20 and count $^{33}$P cpm on scintillation counter.

Calculate percent activity from raw data in cpm $$\text{percent activity} = (\text{sample} - \text{bkg})/(\text{total activity} - \text{bkg}) \times 100$$

Calculate IC$_{50}$ from percent activity, using one-site dose response sigmoidal model $$y = A + ((B-A)/(1+((x/C)^D)))$$

x=cmpd conc, y=% activity, A=min, B=max, C=IC$_{50}$, D=1 (hill slope)

Bruton's Tyrosine Kinase (BTK) Inhibition TR-FRET (Time Resolved FRET) Assay

This BTK competition assay measures compound potency (IC50) for the inactivated state of Bruton's Tyrosine Kinase using FRET (Förster/Flouresence Resonance Energy Transfer) technology. The BTK-Eu complex was incubated on ice one hour prior to use at a starting concentration of 50 nM BTK-Bioease™: 10 nM Eu-streptavidin (Perkin-Elmer Catalog# AD0062). The assay buffer consisted of 20 mM HEPES (pH 7.15), 0.1 mM DTT, 10 mM MgCl$_2$, 0.5 mg/ml BSA with 3% Kinase Stabilizer (Fremont Biosolutions, Catalog #STB-K02). After 1 h, the reaction mixture from above was diluted 10 fold in assay buffer to make 5 nM BTK: 1 nM Eu-Streptavidin complex (donor fluorophore). 18 μl of a mixture of 0.11 nM BTK-Eu and 0.11 nM Kinase Tracer 178 (Invitrogen, Catalog #PV5593,) with BTK-Eu alone as no negative control, was then dispensed into 384-well flat bottom plates (Greiner, 784076). Compounds to be tested in assay were prepared as 10× concentrations and serial dilution in half-log increments was performed in DMSO so as to generate 10 point curves. To initiate the FRET reaction, compounds prepared as 10× stock in DMSO was added to the plates and the plates were incubated 18-24 h at 14° C.

After the incubation the plates were read on a BMG Pherastar Fluorescent plate reader (or equivalent) and used to measure the emission energy from the europium donor fluorophore (620 nm emission) and the FRET (665 nm emission). The negative control well values were averaged to obtain the mean minimum. The positive "no inhibitor" control wells were averaged to obtain the mean maximum. Percent of maximal FRET was calculated using following equation:

$$\% \text{ max FRET} = 100 \times [(\text{FSR}_{cmpd} - \text{FSR}_{mean\ min})/(\text{FSR}_{mean\ max} - \text{FSR}_{mean\ min})]$$

where FSR=FRET Signal ratio. % Max FRET curves were plotted in Activity Base (Excel) and the IC50(%), hill slope, z' and % CV were determined. The mean IC50 and standard deviation will be derived from duplicate curves (singlet inhibition curves from two independent dilutions) using Microsoft Excel.

Representative compound data for this assay are listed below in Table II.

TABLE II

| Compound | FRET IC50 (μmol) |
|---|---|
| 1 | 9.57272 |
| 2 | 100 |
| 3 | 2.82172 |
| 4 | 40.6264 |
| 5 | 0.05694 |
| 6 | 0.04532 |
| 7 | 0.109 |

Inhibition of B Cell Activation in Whole Blood Measured by CD69 Expression

A procedure to test the ability of BTK inhibitors to suppress B cell receptor-mediated activation of B cells in human blood is as follows:

Human whole blood (HWB) is obtained from healthy volunteers, with the following restrictions: 24 hr drug-free, non-smokers. Blood is collected by venipuncture into Vacutainer tubes anticoagulated with sodium heparin. Test compounds are diluted to ten times the desired starting drug concentration in PBS (20×), followed by three-fold serial dilutions in 10% DMSO in PBS to produce a nine point dose-response curve. 5.5 μl of each compound dilution is added in duplicate to a 2 ml 96-well V bottom plate (Analytical Sales and Services, #59623-23); 5.5 μl of 10% DMSO in PBS is added to control and no-stimulus wells. HWB (100 μl) is added to each well, and after mixing the plates are incubated at 37 C, 5% CO$_2$, 100% humidity for 30 minutes. Goat F(ab')2 anti-human IgM (Southern Biotech, #2022-14) (10 μl of a 500 μg/ml solution, 50 μg/ml final concentration) is added to each well (except the no-stimulus wells) with mixing and the plates are incubated for an additional 20 hours.

At the end of the 20 hour incubation, samples are incubated with florescent-probe-labeled antibodies (15 μl PE Mouse anti-Human CD20, BD Pharmingen, #555623, and/or 20 μl APC Mouse anti-Human CD69, BD Pharmingen #555533) for 30 minutes, at 37 C, 5% $CO_2$, 100% humidity. Included are induced control, unstained and single stains for compensation adjustments and initial voltage settings. Samples are then lysed with 1 ml of 1× Pharmingen Lyse Buffer (BD Pharmingen #555899), and plates are centrifuged at 1800 rpm for 5 minutes. Supernatants are removed via suction and the remaining pellets are lysed again with another 1 ml of 1× Pharmingen Lyse Buffer, and plates are spun down as before. Supernatants are aspirated and remaining pellets are washed in FACs buffer (PBS+1% FBS). After a final spin, the supernatants are removed and pellets are resuspended in 180 μl of FACs buffer. Samples are transferred to a 96 well plate suitable to be run on the HTS 96 well system on the BD LSR II flow cytometer.

Using appropriate excitation and emission wavelengths for the fluorophores used, data are acquired and percent positive cell values are obtained using Cell Quest Software. Results are initially analyzed by FACS analysis software (Flow Jo). The IC50 for test compounds is defined as the concentration which decreases by 50% the percentage of CD69-positive cells that are also CD20-positive after stimulation by anti-IgM (average of 8 control wells, after subtraction of the average of 8 wells for the no-stimulus background). The IC50 values are calculated using XLfit software version 3, equation 201.

Inhibition of B-Cell Activation—B Cell FLIPR Assay in Ramos Cells

Inhibition of B-cell activation by compounds of the present invention is demonstrated by determining the effect of the test compounds on anti-IgM stimulated B cell responses.

The B cell FLIPR assay is a cell based functional method of determining the effect of potential inhibitors of the intracellular calcium increase from stimulation by an anti-IgM antibody. Ramos cells (human Burkitt's lymphoma cell line. ATCC-No. CRL-1596) were cultivated in Growth Media (described below). One day prior to assay, Ramos cells were resuspended in fresh growth media (same as above) and set at a concentration of $0.5 \times 10^6$/mL in tissue culture flasks. On day of assay, cells were counted and set at a concentration of $1 \times 10^6$/mL1 in growth media supplemented with 1 μM FLUO-3AM (TefLabs Cat-No. 0116, prepared in anhydrous DMSO and 10% Pluronic acid) in a tissue culture flask, and incubated at 37° C. (4% $CO_2$) for one h. To remove extracellular dye, cells were collected by centrifugation (5 min, 1000 rpm), resuspended in FLIPR buffer (described below) at $1 \times 10^6$ cells/mL and then dispensed into 96-well poly-D-lysine coated black/clear plates (BD Cat-No. 356692) at $1 \times 10^5$ cells per well. Test compounds were added at various concentrations ranging from 100 μM to 0.03 μM (7 concentrations, details below), and allowed to incubate with cells for 30 min at RT. Ramos cell $Ca^{2+}$ signaling was stimulated by the addition of 10 μg/mL anti-IgM (Southern Biotech, Cat-No. 2020-01) and measured on a FLIPR (Molecular Devices, captures images of 96 well plates using a CCD camera with an argon laser at 480 nM excitation).

Media/Buffers:

Growth Medium: RPMI 1640 medium with L-glutamine (Invitrogen, Cat-No. 61870-010), 10% Fetal Bovine Serum (FBS, Summit Biotechnology Cat-No. FP-100-05); 1 mM Sodium Pyruvate (Invitrogen Cat. No. 11360-070).

FLIPR buffer: HBSS (Invitrogen, Cat-No. 141175-079), 2 mM $CaCl_2$ (Sigma Cat-No. C-4901), HEPES (Invitrogen, Cat-No. 15630-080), 2.5 mM Probenecid (Sigma, Cat-No. P-8761), 0.1% BSA (Sigma, Cat-No. A-7906), 11 mM Glucose (Sigma, Cat-No. G-7528)

Compound Dilution Details:

In order to achieve the highest final assay concentration of 100 μM, 24 μL of 10 mM compound stock solution (made in DMSO) is added directly to 576 μL of FLIPR buffer. The test compounds are diluted in FLIPR Buffer (using Biomek 2000 robotic pipettor) resulting in the following dilution scheme: vehicle, $1.00 \times 10^{-4}$ M, $1.00 \times 10^{-5}$, $3.16 \times 10^{-6}$, $1.00 \times 10^{-6}$, $3.16 \times 10^{-7}$, $1.00 \times 10^{-7}$, $3.16 \times 10^{-8}$.

Assay and Analysis:

Intracellular increases in calcium were reported using a max-min statistic (subtracting the resting baseline from the peak caused by addition of the stimulatory antibody using a Molecular Devices FLIPR control and statistic exporting software. The $IC_{50}$ was determined using a non-linear curve fit (GraphPad Prism software).

Mouse Collagen-Induced Arthritis (mCIA)

On day 0 mice are injected at the base of the tail or several spots on the back with an emulsion of Type II Collagen (i.d.) in Complete Freund's adjuvant (CFA). Following collagen immunization, animals will develop arthritis at around 21 to 35 days. The onset of arthritis is synchronized (boosted) by systemic administration of collagen in Incomplete Freund's adjuvant (IFA; i.d.) at day 21 Animals are examined daily after day 20 for any onset of mild arthritis (score of 1 or 2; see score description below) which is the signal to boost. Following boost, mice are scored and dosed with candidate therapeutic agents for the prescribed time (typically 2-3 weeks) and dosing frequency, daily (QD) or twice-daily (BID).

Rat Collagen-Induced Arthritis (rCIA)

On day 0, rats are injected with an emulsion of Bovine Type II Collagen in Incomplete Freund's adjuvant (IFA) is injected intradermally (i.d.) on several locations on the back. A booster injection of collagen emulsion is given around day 7, (i.d.) at the base of the tail or alternative sites on the back. Arthritis is generally observed 12-14 days after the initial collagen injection. Animals may be evaluated for the development of arthritis as described below (Evaluation of arthritis) from day 14 onwards. Animals are dosed with candidate therapeutic agents in a preventive fashion starting at the time of secondary challenge and for the prescribed time (typically 2-3 weeks) and dosing frequency, daily (QD) or twice-daily (BID).

Evaluation of Arthritis:

In both models, developing inflammation of the paws and limb joints is quantified using a scoring system that involves the assessment of the 4 paws following the criteria described below:

Scoring:

1=swelling and/or redness of paw or one digit.
2=swelling in two or more joints.
3=gross swelling of the paw with more than two joints involved.
4=severe arthritis of the entire paw and digits.

Evaluations are made on day 0 for baseline measurement and starting again at the first signs or swelling for up to three times per week until the end of the experiment. The arthritic index for each mouse is obtained by adding the four scores of the individual paws, giving a maximum score of 16 per animal.

Rat In Vivo Asthma Model

Male Brown-Norway rats are sensitized i.p. with 100 μg of OA (ovalbumin) in 0.2 ml alum once every week for three weeks (day 0, 7, and 14). On day 21 (one week following last sensitization), the rats are dosed q.d. with either vehicle or compound formulation subcutaneously 0.5 hour before OA aerosol challenge (1% OA for 45 minutes) and terminated 4 or 24 hours after challenge. At time of sacrifice, serum and plasma are collected from all animals for serology and PK, respectively. A tracheal cannula is inserted and the lungs are lavaged 3× with PBS. The BAL fluid is analyzed for total leukocyte number and differential leukocyte counts. Total leukocyte number in an aliquot of the cells (20-100 μl) is determined by Coulter Counter. For differential leukocyte counts, 50-200 μl of the sample is centrifuged in a Cytospin and the slide stained with Diff-Quik. The proportions of monocytes, eosinophils, neutrophils and lymphocytes are counted under light microscopy using standard morphological criteria and expressed as a percentage. Representative inhibitors of BTK show decreased total leucocyte count in the BAL of OA sensitized and challenged rats as compared to control levels.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

The invention claimed is:

1. A compound of Formula 1,

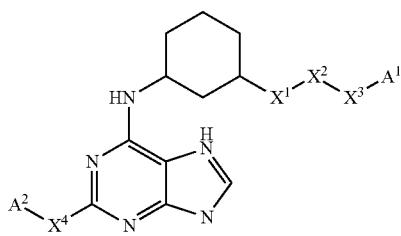

I wherein:
$A^1$ is H or $A^{1'}$;
$A^{1'}$ is lower alkyl or phenyl, optionally substituted with one or more $A^{1''}$;
each $A^{1''}$ is independently halo or lower alkyl;
$A^2$ is H or $A^{2'}$;
$A^{2'}$ is a monocyclic heteroaryl, optionally mono-substituted with tower alkyl;
$X^1$ is —NH, C(=O), or absent;
$X^2$ is —NH, C(=O), or absent;
$X^3$ is lower alkylene or absent; and
$X^4$ is —NH or absent;
or a pharmaceutically acceptable salt thereof,
with the proviso that $A^2$ is $A^{2'}$ and $X^4$ is —NH when $X^1$, $X^2$ and $X^3$ are absent and $A^1$ is H.

2. The compound of claim 1, wherein $X^1$ is —NH.
3. The compound of claim 1, wherein $X^2$ is —C(=O).
4. The compound of claim 1, wherein $X^3$ is absent.
5. The compound of claim 1, wherein $A^1$ is phenyl, optionally substituted with one or more $A^{1''}$.
6. The compound of claim 1, wherein $X^4$ is absent.
7. The compound of claim 1, wherein $A^2$ is H.
8. The compound of claim 1, wherein $X^1$ is —C(=O).
9. The compound of claim 8, wherein $X^2$ is —NH.
10. The compound of claim 1, wherein $X^3$ is methylene.
11. The compound of claim 1, wherein $A^1$ is phenyl, optionally substituted with one or more $A^{1''}$.
12. The compound of claim 1, wherein $X^4$ is —NH, $A^2$ is pyrazolyl, and $A^{2'}$ is methyl.
13. The compound of claim 1, selected from the group consisting of:
  4-tert-butyl-N-[3-(7H-purin-6-ylamino)cyclohexyl]benzamide;
  N-[(3-chlorophenyl)methyl]-3-(9H-purin-6-ylamino)cyclohexane-1-carboxamide;
  6-N-cyclohexyl-2-N-(1-methylpyrazol-4-yl)-9H-purine-2,6-diamine;
  6-N-(3-methylcyclohexyl)-2-N-(1-methylpyrazol-4-yl)-9H-purine-2,6-diamine; and
  4-tert-butyl-N-[3-[[2-[(1-methylpyrazol-4-yl)amino]-9H-purin-6-yl]amino]cyclohexyl]benzamide.
14. The compound of claim 1, selected from the group consisting of:
  4-tert-Butyl-N-[3-(9H-purin-6-ylamino)-cyclohexyl]-benzamide;
  3-(9H-Purin-6-ylamino)-cyclohexanecarboxylic acid 3-chloro-benzylamide,
  N*6*-Cyclohexyl-N*2*-(1-methyl-1H-pyrazol-4-yl)-9H-purine-2,6-diamine;
  N*6*-(3-Methyl-cyclohexyl)-N*2*-(1-methyl-1H-pyrazol-4-yl)-9H-purine-2,6-diamine; and
  4-tert-Butyl-N-{3-[2-(1-methyl-1H-pyrazol-4-ylamino)-9H-purin-6-ylamino]-cyclohexyl}-benzamide.
15. A method for treating rheumatoid arthritis, comprising the step of administering to a patient in need thereof a therapeutically effective amount of a compound of claim 1 or a pharmaceutically acceptable salt thereof.
16. A method for treating asthma, comprising the step of administering to a patient in need thereof a therapeutically effective amount of a compound of claim 1 or a pharmaceutically acceptable salt thereof.
17. A pharmaceutical composition, comprising a therapeutically effective amount of a compound of claim 1, or a pharmaceutically acceptable salt thereof, admixed with at least one pharmaceutically acceptable carrier, excipient or diluent.

* * * * *